US00PP36458P2

(12) United States Plant Patent
van Dijk

(10) Patent No.: US PP36,458 P2
(45) Date of Patent: Feb. 18, 2025

(54) ***HYDRANGEA* PLANT NAMED 'HICANA14'**

(50) Latin Name: *Hydrangea macrophylla*
Varietal Denomination: HICANA14

(71) Applicant: Roy Robin van Dijk, De Lier (NL)

(72) Inventor: Roy Robin van Dijk, De Lier (NL)

(73) Assignee: HI BREEDING B.V., De Lier (NL)

( * ) Notice: Subject to any disclaimer, the term of this patent is extended or adjusted under 35 U.S.C. 154(b) by 0 days.

(21) Appl. No.: 18/534,603

(22) Filed: Dec. 9, 2023

(51) Int. Cl.
*A01H 5/02* (2018.01)
*A01H 6/48* (2018.01)

(52) U.S. Cl.
USPC ..... Plt./250
CPC ..... *A01H 6/48* (2018.05)

(58) Field of Classification Search
USPC ..... Plt./250
CPC ..... A01H 6/48; A01H 5/02
See application file for complete search history.

*Primary Examiner* — Keith O. Robinson
(74) *Attorney, Agent, or Firm* — C. Anne Whealy

(57) ABSTRACT

A new and distinct cultivar of *Hydrangea* plant named 'HICANA14', characterized by its upright and broadly spreading plant habit; moderately vigorous and moderate growth rate; freely branching habit; strong and sturdy stems; dark green-colored leaves; freely flowering habit; large and dense mophead inflorescences with purplish red-colored sterile flowers; and good post-production longevity.

2 Drawing Sheets

Figure 1:
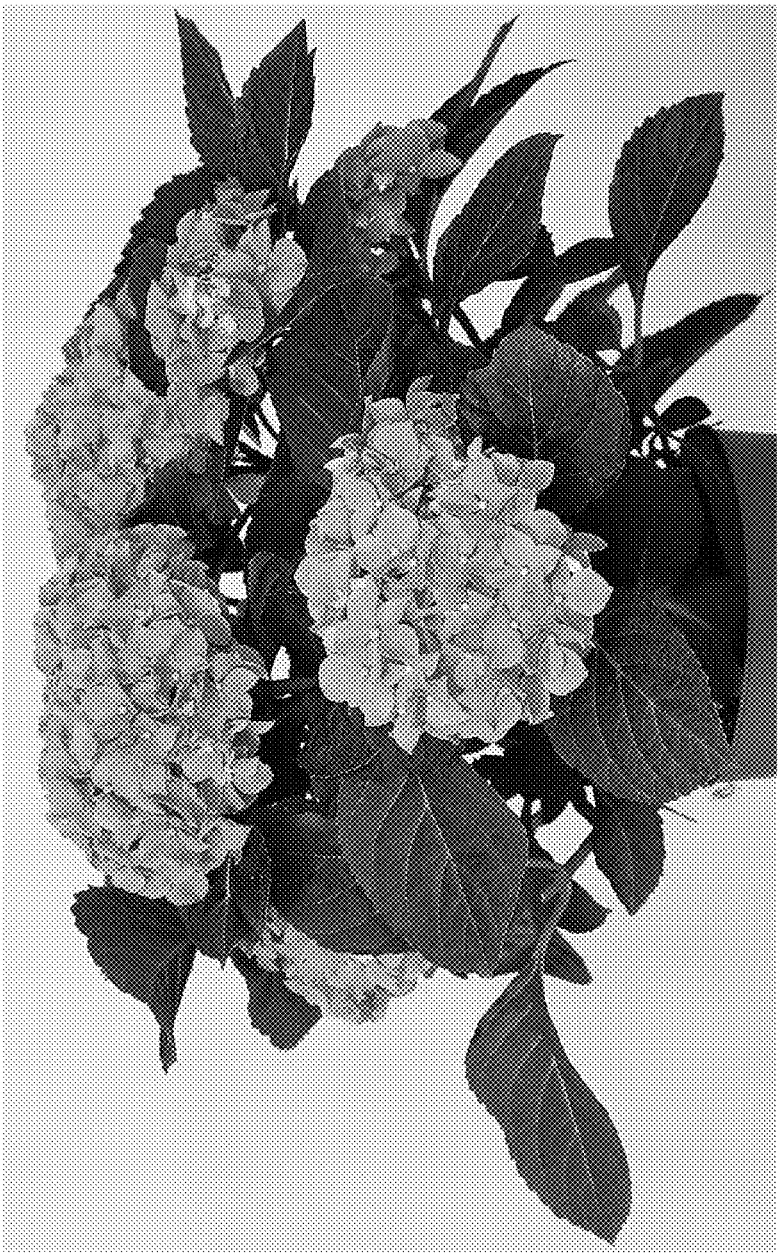

Botanical designation: *Hydrangea macrophylla.*
Cultivar denomination: 'HICANA14'.

STATEMENT REGARDING PRIOR DISCLOSURES BY INVENTOR/APPLICANT & ASSIGNEE

An United Kingdom Plant Breeder's Rights application for the instant plant was filed by the Assignee of the instant application, Hi Breeding B.V. of De Lier, The Netherlands on Nov. 11, 2022, application number 23/800. Foreign priority is not claimed to this United Kingdom Plant Breeder's Rights application.

An European Community Plant Breeder's Rights application for the instant plant was filed by the Assignee of the instant application, Hi Breeding B.V. of De Lier, The Netherlands on Jul. 4, 2023, application number 2023/1462. Foreign priority is not claimed to this European Plant Breeder's Rights application.

The Inventor/Applicant and Assignee assert that no sales, offers for sale or public distribution of the instant plant occurred more than one year prior to the effective filing date of this application.

Any information about the claimed plant would have been obtained from a direct or indirect disclosure from the Inventor/Applicant and/or Assignee. Inventor/Applicant and Assignee claim a prior art exception under 35 U.S.C. 102 (b)(1) for disclosures and/or sales prior to the filing date but less than one year prior to the effective filing date.

BACKGROUND OF THE INVENTION

The present invention relates to a new and distinct cultivar of *Hydrangea* plant, botanically known as *Hydrangea macrophylla*, commercially referred to as a mophead-type *Hydrangea* and hereinafter referred to by the name 'HICANA14'.

The new *Hydrangea* plant is a product of a planned breeding program conducted by the Inventor in De Lier, The Netherlands. The objective of the breeding program is to create new sturdy and strong *Hydrangea* plants with attractive inflorescences and good postproduction longevity.

The new *Hydrangea* plant originated from a cross-pollination in April 2017 of a proprietary selection of *Hydrangea macrophylla* identified as code number 1563, not patented, as the female, or seed, parent with a proprietary selection of *Hydrangea macrophylla* identified as code number 1794, not patented, as the male, or pollen, parent. The new *Hydrangea* plant was discovered and selected as a single flowering plant from within the progeny of the stated cross-pollination in a controlled greenhouse environment in De Lier, The Netherlands in April 2019.

Asexual reproduction of the new *Hydrangea* plant by terminal vegetative cuttings since July 2019 in a controlled greenhouse environment in De Lier, The Netherlands has shown that the unique features of this new *Hydrangea* plant are stable and reproduced true to type in successive generations of asexual reproduction.

SUMMARY OF THE INVENTION

Plants of the new *Hydrangea* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'HICANA14'. These characteristics in combination distinguish 'HICANA14' as a new and distinct *Hydrangea* plant:

1. Upright and broadly spreading plant habit.
2. Moderately vigorous and moderate growth rate.
3. Freely branching habit.
4. Strong and sturdy stems.

5. Dark green-colored leaves.
6. Freely flowering habit.
7. Large and dense mophead inflorescences with purplish red-colored sterile flowers.
8. Good post-production longevity.

Plants of the new *Hydrangea* can be compared to plants of the female parent selection. Plants of the new *Hydrangea* differ primarily from plants of the female parent selection in the following characteristics:

1. Plants of the new *Hydrangea* have sturdier stems than plants of the female parent selection.
2. Sterile flowers of plants of the new *Hydrangea* are purplish red in color whereas sterile flowers of plants of the female parent selection are purplish pink in color.

Plants of the new *Hydrangea* can be compared to plants of the male parent selection. Plants of the new *Hydrangea* differ primarily from plants of the male parent selection in the following characteristics:

1. Plants of the new *Hydrangea* are more vigorous than plants of the male parent selection.
2. Plants of the new *Hydrangea* have sturdier stems than plants of the male parent selection.

Plants of the new *Hydrangea* can be compared to plants of *Hydrangea macrophylla* 'HBA 202911', not patented. In side-by-side comparisons, plants of the new *Hydrangea* differ primarily from plants of 'HBA 202911' in stem strength as stems of plants of the new *Hydrangea* are sturdier than stems of plants of 'HBA 202911'. In addition, sterile flowers of plants of the new *Hydrangea* are purplish red in color whereas sterile flowers of plants of 'HBA 202911' are purplish pink in color.

BRIEF DESCRIPTION OF THE PHOTOGRAPHS

The accompanying colored photographs illustrate the unique appearance of the new *Hydrangea* plant showing the colors as true as it is reasonably possible to obtain in colored reproductions of this type. Colors in the photographs may differ from the color values cited in the detailed botanical description which accurately describe the colors of the new *Hydrangea* plant.

The photograph on the first sheet (FIG. 1) is a side perspective view of a typical flowering plant of 'HICANA14' grown in a container.

Figure 2:
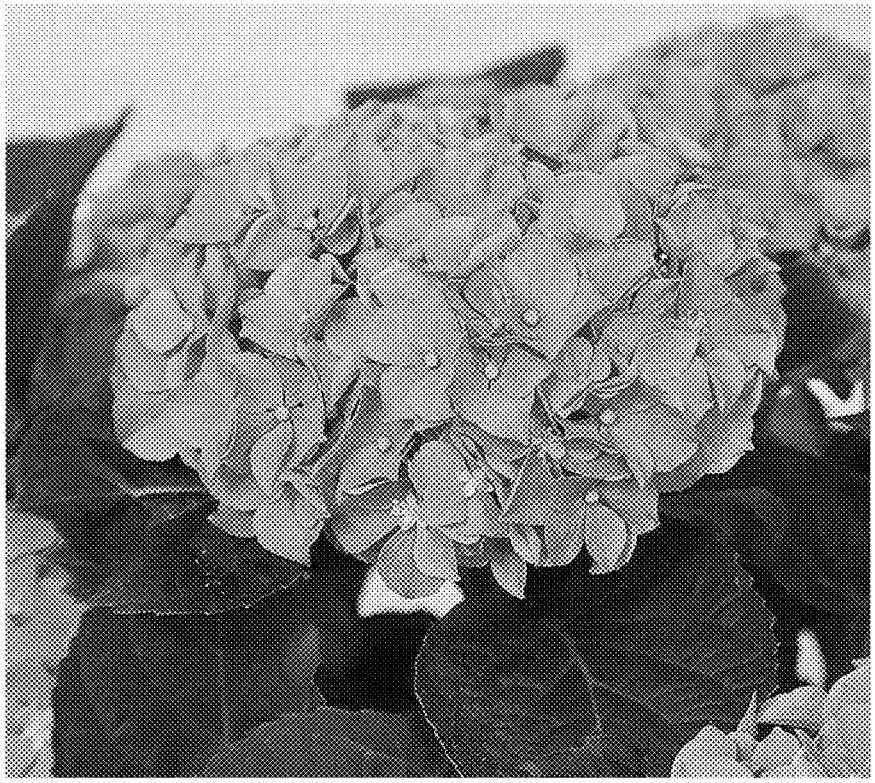

The photograph on the top of the second sheet (FIG. 2) is a close-up view of a typical flowering plant of 'HICANA14'.

DETAILED BOTANICAL DESCRIPTION

Plants used in the aforementioned photographs and in the following description were grown during the late summer in 13-cm containers in a glass-covered greenhouse in De Lier, The Netherlands and under cultural practices typical of commercial *Hydrangea* production. During the production of the plants, day temperatures ranged from 20 C to 35 C, night temperatures ranged from 10 C to 22 C and light levels averaged 4,000 lux. Plants of the new *Hydrangea* were pinched one time and were 18 months old when the photographs and description were taken. In the following description, color references are made to The Royal Horticultural Society Colour Chart, 2015 Edition, except where general terms of ordinary dictionary significance are used. Plants of the new *Hydrangea* can be treated with aluminum sulfate to "blue" the flower color.

Botanical description: *Hydrangea macrophylla* 'HICANA14'.

Parentage:

*Female, or seed, patent*.—Proprietary selection of *Hydrangea macrophylla* identified as code number 1563, not patented.

*Male, or pollen, patent*.—Proprietary selection of *Hydrangea macrophylla* identified as code number 1794, not patented.

Propagation:

*Type cutting*.—By vegetative terminal cuttings.

*Time to initiate roots, summer*.—About twelve days at temperatures about 22 C.

*Time to initiate roots, winter*.—About 14 days at temperatures about 20 C.

*Time to produce a rooted young plant, summer*.—About 28 days at temperatures about 22 C.

*Time to produce a rooted young plant, winter*.—About 30 days at temperatures about 19 C.

*Root description*.—Medium in thickness, fibrous; typically white in color, actual color of the roots is dependent on substrate composition, water quality, fertilizer type and formulation, substrate temperature and physiological age of roots.

*Rooting habit*.—Moderately freely branching; medium density.

Plant description:

*Plant and growth habit*.—Upright, broadly outwardly spreading and mounding plant habit; flattened globular to broadly obovate in overall shape; strong and sturdy stems; moderately vigorous growth habit and moderate growth rate; about six months from propagation are required to produce small finished flowering plants.

*Plant height*.—About 27.8 cm.

*Plant diameter or area of spread*.—About 44 cm.

Lateral branch description:

*Branching habit*.—Freely branching habit with about twelve lateral branches per plant; pinching enhances lateral branch development.

*Length*.—About 13.6 cm.

*Diameter*.—About 5 mm.

*Internode length*.—About 5.6 cm.

*Strength*.—Strong, sturdy.

*Aspect*.—About 30 to 90 degrees from vertical.

*Texture*.—Smooth, glabrous; becoming woody with development.

*Color, developing*.—Close to 144A to 144B.

*Color, fully developed*.—Close to 144A; when woody, close to 199A, N199C and N199D.

*Lenticels*.—Density: Sparse to moderate. Length: About 1.5 mm. Diameter: About 0.5 mm. Color: Close to 200C and 200D.

Leaf description:

*Arrangement*.—Opposite, simple.

*Length*.—About 10.3 cm.

*Width*.—About 8.1 cm.

*Shape*.—Broadly elliptic to broadly obovate.

*Apex*.—Apiculate.

*Base*.—Short attenuate to attenuate.

*Margin*.—Dentate-serrate to coarsely dentate-serrate.

*Texture, upper surface*.—Slightly rugose, glabrous.

*Texture, lower surface*.—Moderately rugose, glabrous.

*Venation pattern*.—Pinnate.

*Color*.—Developing leaves, upper surface: Close to a blend of 137A and 143A. Developing leaves, lower surface: Close to a blend of 146B and 147B. Fully developed leaves, upper surface: Slightly darker than a blend of NN137A and 147A; venation, close to 146D. Fully developed leaves, lower surface: Close to 147A; venation, close to 145A.

*Petioles*.—Length: About 2.7 cm. Diameter: About 2.5 mm to 3.5 mm. Texture and luster, upper and lower surfaces: Smooth, glabrous; moderately glossy. Color, upper surface: Close to 146B to 146C. Color, lower surface: Close to 144A.

Flower description:

*Flower type and habit*.—Showy rotate sterile flowers and small, inconspicuous rotate fertile flowers arranged on mophead-type terminal panicles; panicles flattened globular in shape; sterile flowers face upright to outwardly and fertile flowers face mostly upright.

*Fragrance*.—None detected.

*Natural flowering season*.—In the garden, plants flower continuously from the late spring to late summer in The Netherlands; flower dormancy can be broken with a cold storage treatment.

*Flower longevity*.—Good postproduction longevity; sterile flowers maintain good substance for about six weeks on the plant, sterile flowers persistent; fertile flowers last for a few days on the plant, fertile flowers not persistent.

*Quantity of flowers*.—Freely flowering habit; about 320 sterile flowers per panicle and about 20 fertile flowers per panicle.

*Panicle height*.—About 8.5 cm.

*Panicle diameter*.—About 14 cm.

*Panicle peduncles*.—Length: About 6.3 cm. Diameter: About 3.75 mm. Strength: Strong. Aspect: Primary peduncles, mostly erect; lateral peduncles, about 35 degrees from primary peduncle axis. Texture: Sparsely to moderately pubescent. Color: Close to 144B; distally, tinged with close to a blend of 64D and 70C.

*Sterile flower buds*.—Length: About 1 cm. Diameter: About 1.7 cm. Shape: Broadly cup-shaped. Color: Close to 58D; towards the base, close to 150C to 150D; when "blued", close to N88C and towards the base, close to 154D.

*Fertile flower buds*.—Length: About 3 mm. Diameter: About 3.5 mm. Shape: Flattened globular. Color: Close to 62B to 62C; when "blued", close to 97A.

*Sterile flower diameter*.—About 2.6 cm to 3.4 cm.

*Sterile flower depth* (*height*).—About 8 mm to 13 mm.

*Fertile flower diameter*.—About 9 mm.

*Fertile flower depth* (*height*).—About 9 mm.

*Petals, sterile flowers*.—Quantity and arrangement: Four, or occasionally five, in a single whorl. Length: About 3.5 mm. Width: About 2.25 mm. Shape: Ovate, moderately concave. Apex: Acute. Base: Cuneate. Margin: Entire. Texture and luster, upper and lower surfaces: Smooth, glabrous; matte. Color: When opening, upper surface: Close to 73C and towards the base, close to 73D; when "blued", close to 98C. When opening, lower surface: Close to 73C; when "blued", close to 98C. Fully opened, upper and lower surfaces: Close to 73D; when "blued", close to 98C to 98D; color does not change with subsequent development.

*Petals, fertile flowers*.—Quantity and arrangement: About five in a single whorl. Length: About 5 mm. Width: About 3 mm. Shape: Ovate, concave. Apex: Acute. Base: Cuneate. Margin: Entire. Texture and luster, upper and lower surfaces: Smooth, glabrous; matte. Color: When opening, upper surface: Close to 73D; when "blued", close to 100C to 100D. When opening, lower surface: Close to 73D; when "blued", close to 115D. Fully opened, upper surface: Close to 73D; when "blued", close to 100D; color does not change with subsequent development. Fully opened, lower surface: Close to 73D; when "blued", close to 115D; color does not change with subsequent development.

*Sepals, sterile flowers*.—Quantity and arrangement: Typically four or five, or rarely six, in a single whorl; slightly to strongly imbricate. Length: About 1.6 cm. Width: About 1.6 cm. Shape: Broadly ovate to rhomboidal; slightly concave. Apex: Broadly to bluntly acute. Base: Cuneate. Margin: Entire; coarsely undulate. Texture and luster, upper and lower surfaces: Smooth, glabrous; matte. Color: When opening, upper surface: Close to 63B; when "blued", close to N87C. When opening, lower surface: Close to 64D; when "blued", close to 85A. Fully opened, upper surface: Close to a blend of 63B and 63C; towards the base, close to 68B; when "blued", close to 97A and tinged towards the base with close to N82B to N82C; color does not change with subsequent development. Fully opened, lower surface: Close to 65A; when "blued", close to 94D and tinged towards the base with close to 77C; color does not change with subsequent development.

*Sepals, fertile flowers*.—Quantity and arrangement: Five in a single whorl. Length: About 2.5 mm. Width: About 1.5 mm. Shape: Ovate. Apex: Acute. Base: Cuneate. Margin: Entire. Texture and luster, upper and lower surfaces: Smooth, glabrous; matte. Color: When opening, upper surface: Close to 68C; when "blued", close to 92B. When opening, lower surface: Close to 68D; when "blued", close to 138D. Fully opened, upper surface: Close to 68C; when "blued", close to 92B to 92C; color does not change with subsequent development. Fully opened, lower surface: Close to 68D; when "blued", close to 138D; color does not change with subsequent development.

*Pedicels, sterile flowers*.—Length: About 1.7 cm. Diameter: About 1.25 mm. Strength: Moderately strong. Aspect: About 30 degrees from main peduncle axis Texture and luster: Moderately pubescent; matte. Color: Close to a blend of 64D and 70C; when "blued", close to N88C.

*Pedicels, fertile flowers*.—Length: About 4.5 mm. Diameter: About 0.1 mm. Strength: Moderately strong. Aspect: About 5 degrees from vertical. Texture and luster: Moderately pubescent; matte. Color: Close to 68D; when "blued", close to 98C.

*Reproductive organs, sterile flowers*.—Stamens: Quantity per flower: About ten. Filament length: About 3 mm. Filament color: Close to 69D; when "blued", close to 92D. Anther length: About 0.5 mm. Anther shape: Broadly oblong. Anther color: Close to 69C;

when "blued", close to 97B to 97C. Pollen amount: Moderate. Pollen color: Close to 156A. Pistils: Pistil quantity per flower: About one to three. Pistil length: About 1.5 mm. Stigma shape: Club-shaped. Stigma color: Close to 69D; when "blued", close to 188D. Style length: About 1 mm. Style color: Close to 69C; when "blued", close to 188D. Ovary color: Close to 157D; when "blued", close to 145D.

*Reproductive organs, fertile flowers*.—Stamens: Quantity per flower: About ten. Filament length: About 5 mm. Filament color: Close to N155D; when "blued", close to N155A. Anther length: About 5 mm. Anther shape: Broadly oblong. Anther color: Close to 69C; when "blued", close to 97B to 97C. Pollen amount: Moderate. Pollen color: Close to 156A. Pistils: Pistil quantity per flower: About three, occasionally two or four. Pistil length: About 1.5 mm. Stigma shape: Club-shaped. Stigma color: Close to 69D; when "blued", close to 188D. Style length: About 1 mm. Style color: Close to 69C; when "blued", close to 188D. Ovary color: Close to 157D; when "blued", close to 145D.

*Seeds*.—To date, seed development has not been observed on plants of the new *Hydrangea*.

Pathogen & pest resistance: Plants of the new *Hydrangea* have been observed to be tolerant to *Botrytis* (*Botrytis cinerea*). To date, plants of the new *Hydrangea* have not been observed to be resistant to pests and other pathogens common to *Hydrangea* plants.

Temperature tolerance: Plants of the new *Hydrangea* have been shown to be suitable for USDA Hardiness Zones 5 through 9.

It is claimed:

1. A new and distinct *Hydrangea* plant named 'HICANA14' as illustrated and described.

* * * * *